United States Patent [19]

Klainer et al.

[11] Patent Number: 5,109,442
[45] Date of Patent: Apr. 28, 1992

[54] WATERPROOF OPTICAL FIBER CHEMICAL SENSOR AND METHOD OF MAKING SAME

[75] Inventors: Stanley M. Klainer; Dileep K. Dandge; Kisholoy Goswami, all of Henderson, Nev.

[73] Assignee: FiberChem Inc., Las Vegas, Nev.

[21] Appl. No.: 501,146

[22] Filed: Mar. 28, 1990

[51] Int. Cl.$^5$ .................. G02B 6/02; G01N 21/00; H01J 5/16; A61B 5/00
[52] U.S. Cl. ...................... 385/12; 385/123; 385/145; 422/82.11; 427/163; 250/227.11; 250/227.14; 128/634; 252/582; 210/500.25; 210/500.27
[58] Field of Search ............... 350/96.29, 96.30, 96.34, 350/96.15, 320, 96.33; 356/39, 42; 422/68.1, 82.05, 82.06, 82.08, 82.11; 128/634, 636, 637; 250/227.11, 227.14; 427/163; 252/582, 586, 589; 210/500.21, 500.27, 500.25, 500.35, 500.36, 505, 506

[56] References Cited

U.S. PATENT DOCUMENTS

| | | | |
|---|---|---|---|
| 4,682,895 | 7/1987 | Costello | 350/96.29 |
| 4,842,783 | 6/1989 | Blaylock | 264/1.4 |
| 4,913,519 | 4/1990 | Klainer et al. | 350/96.29 |
| 4,919,891 | 4/1990 | Yafuso et al. | 422/58 |
| 4,925,268 | 5/1990 | Iyer et al. | 350/96.29 |
| 4,929,049 | 5/1990 | Le Goullon et al. | 350/96.29 |
| 4,950,405 | 8/1990 | Miyasaka et al. | 210/500.28 |
| 4,974,929 | 12/1990 | Curry | 350/96.29 |
| 4,999,306 | 3/1991 | Yafuso et al. | 350/96.30 |
| 5,026,139 | 6/1991 | Klainer et al. | 350/96.29 |
| 5,028,395 | 7/1991 | Sebille et al. | 350/96.29 X |
| 5,036,194 | 7/1991 | Hazel | 350/96.29 X |

Primary Examiner—Brian Healy
Attorney, Agent, or Firm—Henry P. Sartorio

[57] ABSTRACT

A fiber optic chemical sensor is made water repellent by attaching a plurality of long, hydrophobic chains, e.g. silane polymers, to the surface. The chains extend from the surface and form a semi-permeable barrier which repels water molecules while selectively passing analyte molecules therethrough. In one configuration, the hydrophobic chains are attached substantially uniformly over the clad. In a second configuration, the clad is a plurality of spaced stripes with the hydrophobic chains attached in the gaps between the stripes. In another configuration, a patterned hydrophobic coating of alternating thick and thin segments is formed on the clad.

20 Claims, 1 Drawing Sheet

WATERPROOF OPTICAL FIBER CHEMICAL SENSOR AND METHOD OF MAKING SAME

BACKGROUND OF THE INVENTION

The invention relates generally to fiber optic chemical sensors (FOCS) and more particularly to water repellent FOGS.

A fiber optic is an optical waveguide which transmits light by total internal reflection at the core/clad interface, which occurs when the refractive index of the clad is less than the index of the core. Optical fibers have been used in a wide variety of sensors, known as "optrodes" or "fiber optic chemical sensors" (FOCS), which can detect various chemical species or physical parameters.

U.S. patent application Ser. No. 150,197, filed Jan. 29, 1988, now U.S. Pat. No. 4,929,049, issued May 29, 1990, describes a refractive index FOCS in which a thin film metal clad is formed on the core of sufficient thickness so that analyte molecules adsorbed on the metal clad produce a localized change in refractive index which modulates light transmission through the core. A problem exists when using the refractive index FOCS in an aqueous medium because of the high affinity of the water molecules for the metal clad, which interferes with the measurement. In other words, the FOCS responds to both vapor and liquid water in a manner similar to a non-aqueous analyte.

Accordingly, it would be desirable to make a FOCS, particularly a refractive index FOCS, substantially water repellent while maintaining its sensing characteristics.

The science of making surfaces water repellent is very old. In the modern scientific approach, hydrophobic materials such as silicon-based organometallic polymers, polytetrafluorethylene (Teflon—a registered trademark of DuPont), and the like are applied to the surface by using a variety of techniques to make surfaces water repellent. However, these techniques are generally not applicable to FOCS as it is necessary to impart water repellency while allowing analyte molecules to reach the sensing surface.

SUMMARY OF THE INVENTION

Accordingly, it is an object of the invention to provide a water repellent FOCS.

It is also an object of the invention to provide a water repellent FOCS which does not negatively affect the sensing characteristics of the FOCS.

It is another object of the invention to provide a FOCS which shown little or no response to water vapor or liquid water compared to its response to an analyte of interest.

It is a further object of the invention to provide a water repellent refractive index FOCS.

The invention is a water repellent FOCS and a method of making the same. The surface of the FOCS is made water repellent while keeping intact the sensing characteristics of the FOCS for desired analytes. Hydrophobic polymers are attached to the surface of the FOCS (i.e. the clad or permeable outer sensing layer). The polymers extend out from the surface in long chains like tentacles and form a loose mesh covering the surface which repels water but allows the analyte of interest to pass through the polymer chains. In an alternate embodiment, the FOCS is formed with a striped clad, and the polymer chains are attached to the FOCS in the gaps between the clad stripes. In still another embodiment, a fiber optic core with sensing clad material is completely covered by hydrophobic material, first with thick spaced segments, and then with a thin layer which fills the gaps between the thick segments.

DETAILED DESCRIPTION OF THE PREFERRED EMBODIMENTS

Figure 1:
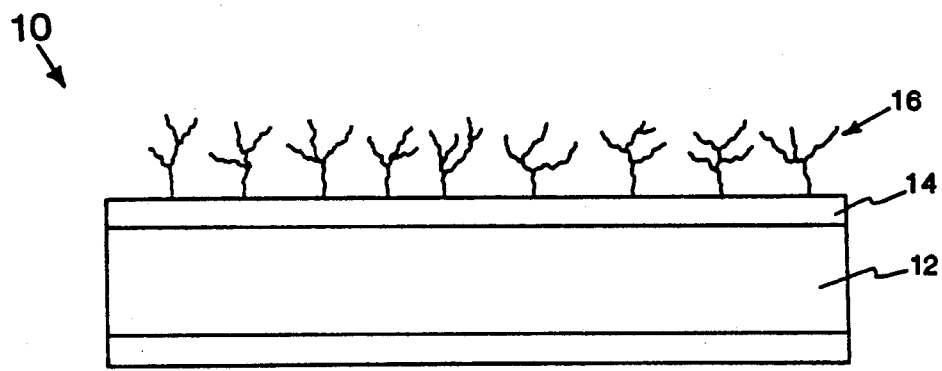
FIG. 1 is a sectional view of a FOCS with water-repelling, hydrophobic chains attached to the surface.

As shown in FIG. 1, a FOCS 10 has a fiber optic core 12 surrounded by a clad 14. FOCS 10 may be a refractive index FOCS in which clad 14 is a thin film metal clad, as described in U.S. patent application Ser. No. 150,197, filed Jan. 29, 1988, now U.S. Pat. No. 4,929,049, issued May 29, 1990, which is herein incorporated by reference. Alternatively, FOCS 10 may be another type of FOCS in which clad 14 is of a specific chemistry which reacts with an analyte of interest. In addition, FOCS 10 could be more than a two layer structure, e.g., a sandwich structure as described in U.S. Pat. No. 4,846,548, issued Jul. 11, 1989, which is herein incorporated by reference.

FOCS 10 is made water repellent by attaching a plurality of long, hydrophobic chains 16 to the surface thereof, i.e., to the surface of clad 14. These long, hydrophobic chains 16 extend like tentacles and form a loose mesh over the surface of FOCS 10. The chains are sufficiently long and dense and, in some instances, are sufficiently cross-linked to provide a water repellent barrier around FOCS 10. However, the water repellent barrier formed by the long, hydrophobic chains do not prevent the analyte of interest from contacting FOCS 10. Thus, the long, hydrophobic chains form a selective water repellent barrier which does not interfere with the sensing capability of the FOCS. The hydrophobic chains attached to the surface of the FOCS selectively repel water molecules in either vapor or liquid phase and provide sufficient porosity to pass the desired molecules to the FOCS surface.

The basic feature of the water repellent FOCS is a hydrophobic coating which repels water while allowing the FOCS to react with the target molecules. The hydrophobic coating is deposited so that there are holes in the coating, or alternatively as stripes, wherein the holes or stripes are small enough so the hydrophobic groups can work against the water molecules but large enough for the target molecules to reach the sensor. Thus, the hydrophobic molecular structure is matched to the size/shape of the target molecules.

The long, hydrophobic chains are polymers, e.g. alkyltrialkoxysilanes such as octadecyltrimethoxysilane or octyltrimethyloxysilane and polymers derived from these compounds. Also included are polymeric silanes with general structure

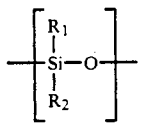

where $R_1$ and $R_2$ are each selected from alkyl, alkylaryl or aryl group and in particular $R_1$ or $R_2$=alkyl=$C_1$ to $C_6$ chain, and
$R_1$ or $R_2$=aryl=phenyl, tolyl, benzyl Also included are polymers such as DuPont-Teflon, DuPont-Tefzel and copolymers of tetrafluorethylene with monomers such as partially fluorinated or completely fluorinated alkyl or aryl or alkyaryl vinyl ethers or vinyl esters. An example of such a copolymer is given by

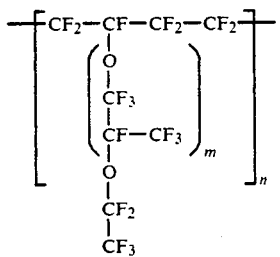

The polymers are attached to the FOCS surface by any suitable technique. In a preferred method, 0.1 to 20% solutions (weight by volume), and more preferably 5 to 10% solutions of the polymers in water are prepared. The FOCS is immersed in the solution and heated to 25°-100° C., and more preferably between 60°-90° C., for 0-3 hours. The solution is cooled, and the FOCS removed and further cured in an oven for 2-120 minutes, and more preferably 15-60 minutes.

Figure 2:
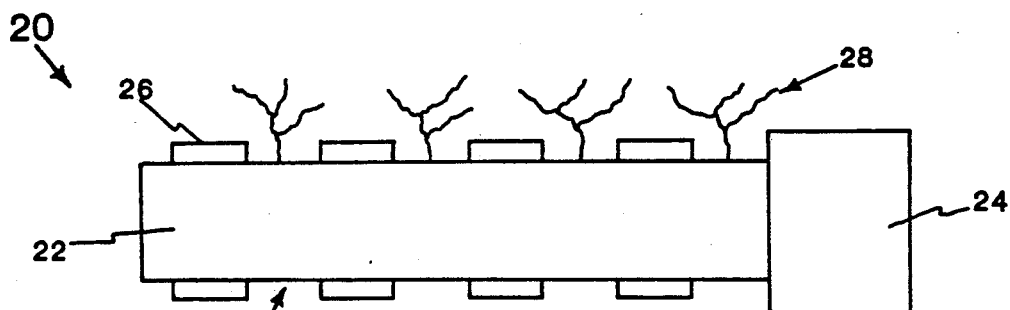
FIG. 2 is a sectional view of a FOCS with a striped clad and water-repelling, hydrophobic chains attached in the gaps between the clad stripes.

In an alternate embodiment of the invention shown in FIG. 2, a FOCS 20 has a fiber optic core 22 with a fluorescent tip 24 at one end thereof. Clad 26 is formed of a plurality of spaced stripes, e.g. of platinum metal. Long, hydrophobic chains 28 are attached to FOCS 20 in the gaps 30 between clad stripes 26. The long, hydrophobic chains are again polymers, e.g. silanes, as previously described. The structure can be formed using complementary masks. A first mask is used to deposit clad stripes 26 on core 22. A second (complementary) mask is used to coat FOCS 22 with the hydrophobic chains to attach the chains only in gaps 30 and not on clad stripes 26. The long chains extend over the metal stripes from the gaps (but do not bond to the metal stripes) and form a selective barrier which selectively repels water while passing the desired molecules, as previously described.

The striped clads can be formed of the same materials used for the solid (uniform) clads. Platinum is highly sensitive to benzene, toluene, xylene, and other low molecular weight, aromatic hydrocarbons as well as aliphatic hydrocarbons and thus is a particularly useful clad. However, the metal clad stripes can alternately be formed of other metals (including metal compounds and alloys) which are known to be useful for a refractive index FOCS as described in U.S. patent application entitled "Fiber Optic Refractive Index Sensor Using Metal Cladding", Ser. No. 501,144 filed herewith, now U.S. Pat. No. 5,026,139, issued Jun. 25, 1991, which is a CIP of Ser. No. 150,197 filed Jan. 29, 1988, now U.S. Pat. No. 4,929,049, issued May 29, 1990, which are herein incorporated by reference. The clad can also be formed of stripes of organic or organometallic or inorganic sensing material.

Figure 3:
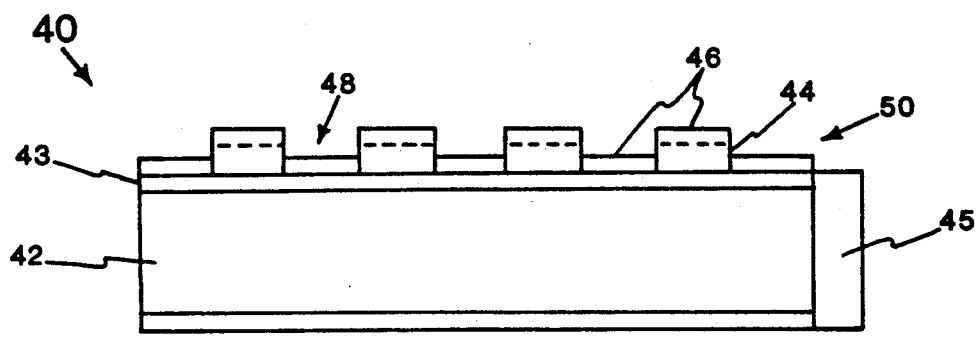
FIG. 3 is sectional view of a FOCS having a clad covered with thick spaced segments of hydrophobic material with a thin layer of hydrophobic material in the gaps between the thick segments.

In a third embodiment of the invention, shown in FIG. 3, FOCS 40 ha a fiber optic core 42 surrounded by a thin film metal clad 43 or other clad. FOCS 40 also has a reflective tip or cap 45. Of course, the linear (dual end) configuration of FIG. 1, fluorescent tip 24 of FIG. 2, and reflective tip 45 of FIG. 3 are interchangeable in any of the embodiments, depending on the particular measurement technique utilized. The optical fiber of the dual end type sensor can be configured in a loop design. Clad 43 is coated with a patterned hydrophobic coating 50 made of a plurality of thick spaced stripes 44 of hydrophobic material followed by a thin layer 46 of hydrophobic material which fills the gaps 48 between thick stripes 44 (while also covering stripes 44). Coating 50 can be formed by first depositing the polymer material in a striped pattern, e.g. using a mask, to form the thick segments 44. A thin layer of the same material is then deposited over the entire structure to form the thin segments 46 in gaps 48 between thick segments 44. The extra amount of material deposited on segments 44 forms a part of segment 44. The hydrophobic coating 50 is made of the same polymers, e.g. silanes, as previously described deposited in thick segments separated by thin segments. FIG. 3 is shown on a more macroscopic scale than FIGS. 1 and 2 so individual polymer chains are not shown, only the overall structure of the hydrophobic coating. The thin segments 46 have sufficient porosity to the desired analyte molecules while repelling water molecules.

The invention thus provides a method for imparting water repellency to FOCS, and a water repellent FOCS. The FOCS is waterproofed by means of a hydrophobic coating which may be deposited substantially uniformly over a clad, or alternatively deposited in stripes between segments of a striped clad, or also deposited in a pattern of alternating thick and thin segments over a clad. The hydrophobic coating is formed for a particular analyte of interest of suitable polymers, having suitable chain length and suitable coating density, to form a semipermeable coating which passes the analyte molecules while repelling water molecules which would interfere with the measurement. In accordance with the invention, the water repellent FOCS shows substantially no response to water vapor or liquid water, and thus is unaffected in its response to the target analyte.

Changes and modifications in the specifically described embodiments can be carried out without departing from the scope of the invention, which is intended to be limited only by the scope of the appended claims.

We claim:

1. A water repellent fiber optic chemical sensor apparatus, comprising:
   a fiber optic chemical sensor having a fiber optic core and a fiber optic clad thereon;
   a plurality of long, hydrophobic chains attached to, and extending from, the surface of the fiber optic chemical sensor to repel water molecules from the sensor surface while selectively allowing preselected analyte molecules to reach the sensor surface;
   wherein the clad is a substantially uniform clad on the surface of the sensor and the hydrophobic chains are attached substantially uniformly over the clad; and wherein the fiber optic chemical sensor is a refractive index sensor in which the clad is a thin metal clad.

2. A water repellent fiber optic chemical sensor apparatus, comprising:

a fiber optic chemical sensor having a fiber optic core and a fiber optic clad thereon;

a plurality of long, hydrophobic chains attached to, and extending from, the surface of the fiber optic chemical sensor to repel water molecules from the sensor surface while selectively allowing preselected analyte molecules to reach the sensor surface;

wherein the clad comprises a plurality of spaced stripes separated by gaps and the hydrophobic chains are attached in the gaps and extend over the clad stripes to substantially cover the clad stripes and repel water molecules from the clad.

3. The apparatus of claim 2 wherein the clad comprises a plurality of thin metal stripes or stripes of organic or organometallic or inorganic sensing material.

4. The apparatus of claim 3 wherein the clad comprises a plurality of thin platinum stripes.

5. The apparatus of claim 1 wherein the hydrophobic chains are silane polymers.

6. A water repellent fiber optic chemical sensor apparatus, comprising:

a fiber optic chemical sensor having a fiber optic core and a fiber optic clad thereon;

a plurality of long, hydrophobic chains attached to, and extending from, the surface of the fiber optic chemical sensor to repel water molecules from the sensor surface while selectively allowing preselected analyte molecules to reach the sensor surface;

wherein the hydrophobic chains are alkyltrialkoxysilane polymers.

7. The apparatus of claim 6 wherein the polymers are octadecyltrimethoxysilane or octyltrimethoxysilane.

8. A water repellent fiber optic chemical sensor apparatus, comprising:

a fiber optic chemical sensor having a fiber optic core and a fiber optic clad thereon;

a plurality of long, hydrophobic chains attached to, and extending from, the surface of the fiber optic chemical sensor to repel water molecules from the sensor surface while selectively allowing preselected analyte molecules to reach the sensor surface;

wherein the hydrophobic chains are silane polymers with the structure

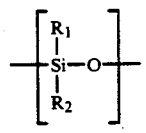

where $R_1$ and $R_2$ are each selected from the group consisting of alkyl, alkylaryl, and aryl.

9. The apparatus of claim 8 wherein $R_1$ and $R_2$ are each selected from $C_1$ to $C_6$ chain alkyl, phenyl, tolyl and benzyl.

10. The apparatus of claim 1 wherein the hydrophobic chains are tetrafluoroethylene polymers.

11. A water repellent fiber optic chemical sensor apparatus, comprising:

a fiber optic chemical sensor having a fiber optic core and a fiber optic clad thereon;

a plurality of long, hydrophobic chains attached to, and extending from, the surface of the fiber optic chemical sensor to repel water molecules from the sensor surface while selectively allowing preselected analyte molecules to reach the sensor surface;

wherein the hydrophobic chains are copolymers of tetrafluorethylene with monomers selected from partially fluorinated or completely fluorinated alkyl or aryl or alkylaryl vinyl ethers or vinyl esters.

12. The apparatus of claim 1 further comprising a fluorescent tip on the fiber optic sensor.

13. The apparatus of claim 1 further comprising a reflective tip on the fiber optic sensor.

14. The apparatus of claim 1 wherein the fiber optic sensor has a dual end configuration with an input end and in output end.

15. A method of making a fiber optic sensor water repellent comprising attaching a plurality of long, hydrophobic chains to a lateral surface of the sensor to repel water molecules while selectively allowing preselected analyte molecules to reach the sensor surface, wherein the hydrophobic chains are selected from (a) alkyltrialkoxysilane polymers,
(b) silane polymers with the structure

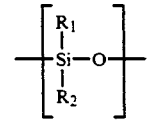

where $R_1$ and $R_2$ are each selected from the group consisting of alkyl, alkylaryl, and aryl, and (c) copolymers of tetrafluoroethylene with monomers selected from partially fluorinated or completely fluorinated alkyl or aryl or alkylaryl vinyl ethers or vinyl esters.

16. The method of claim 15 comprising attaching the hydrophobic chains substantially uniformly to a fiber optic clad of the sensor.

17. A method of making a fiber optic sensor water repellent comprising forming the sensor with a clad comprising a plurality of spaced stripes separated by gaps and attaching a plurality of long, hydrophobic chains in the gaps to repel water molecules while selectively allowing preselected analyte molecules to reach the sensor surface.

18. The method of claim 17 further depositing the clad using a first mask and attaching the hydrophobic chains using a second mask which is complementary to the first mask.

19. A method of making a fiber optic sensor water repellent comprising attaching a plurality of long, hydrophobic chains to a lateral surface of the sensor by forming a patterned coating of alternately thick and thin segments of the hydrophobic chains to repel water molecules while selectively allowing preselected analyte molecules to reach the sensor surface.

20. A water repellent fiber optic chemical sensor apparatus, comprising:

a fiber optic chemical sensor having a fiber optic core and a fiber optic clad thereon;

a plurality of long, hydrophobic chains attached to, and extending rom, the surface of the fiber optic chemical sensor to repel water molecules from the sensor surface while selectively allowing preselected analyte molecules to reach the sensor surface;

wherein the hydrophobic chains form a patterned coating of alternately thick and thin segments of the hydrophobic chains.

* * * * *